United States Patent
Jain et al.

(10) Patent No.: US 9,963,449 B2
(45) Date of Patent: May 8, 2018

(54) PROCESS FOR THE PREPARATION OF PALIPERIDONE PALMITATE

(71) Applicant: AUROBINDO PHARMA LIMITED, Kondapur, Hitech, Telangana, Hyderabad (IN)

(72) Inventors: Sandeep Jain, Hyderabad (IN); Srikanth Sindhanur, Hyderabad (IN); Anil Kumar Jain, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 0 days. days.

(21) Appl. No.: 15/543,987

(22) PCT Filed: Jan. 13, 2016

(86) PCT No.: PCT/IB2016/050136
§ 371 (c)(1),
(2) Date: Jul. 15, 2017

(87) PCT Pub. No.: WO2016/116831
PCT Pub. Date: Jul. 28, 2016

(65) Prior Publication Data
US 2018/0009802 A1  Jan. 11, 2018

(30) Foreign Application Priority Data

Jan. 19, 2015 (IN) .............................. 269/CHE/2015

(51) Int. Cl.
*A01N 43/90* (2006.01)
*A61K 31/519* (2006.01)
*C07D 471/04* (2006.01)

(52) U.S. Cl.
CPC .......... *C07D 471/04* (2013.01); *A61K 31/519* (2013.01)

(58) Field of Classification Search
CPC ........................... A61K 31/519; C07D 471/04
USPC ..................................... 514/259.41; 544/279
See application file for complete search history.

*Primary Examiner* — Jeffrey H Murray
(74) *Attorney, Agent, or Firm* — Jay R. Akhave

(57) ABSTRACT

The present invention relates to a process for the preparation of pure Paliperidone Palmitate, which comprises: (a) providing a solution of Paliperidone Palmitate in an alcoholic solvent; (b) adding the alcoholic solution of Paliperidone palmitate to water or vice versa; and (c) isolating the product to obtain pure Paliperidone Palmitate.

9 Claims, No Drawings

PROCESS FOR THE PREPARATION OF PALIPERIDONE PALMITATE

FIELD OF THE INVENTION

The present invention relates to a process for the preparation of pure Paliperidone palmitate.

BACKGROUND OF THE INVENTION

Paliperidone, chemically named as (±)-3-[2-[4-(6-Fluoro-1,2-benzisoxazol-3-yl)-1-piperidi-nyl]ethyl]-6,7,8,9-tetrahydro-9-hydroxy-2-methyl-4H-pyrido pyrimidin-4-one has a structure of formula I:

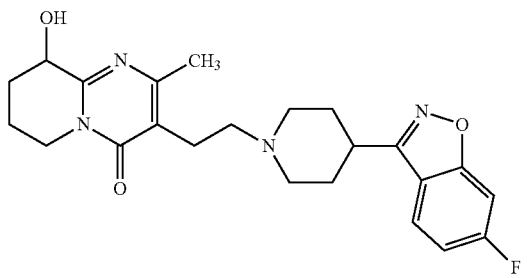

I

Paliperidone is psychotropic agent approved in the United States under the trade name Invega®.

Palmitate ester of Paliperidone, chemically named as (9RS)-3-[2-[4-(6-Fluoro-1,2-benzisoxazol-3-yl)piperidinyl]ethyl]-2-methyl-4-oxo-6,7,8,9-tetrahydro-4H-pyrido-[1,2-a]-pyrimidin-9-yl hexadecanoate has a chemical structure of formula II:

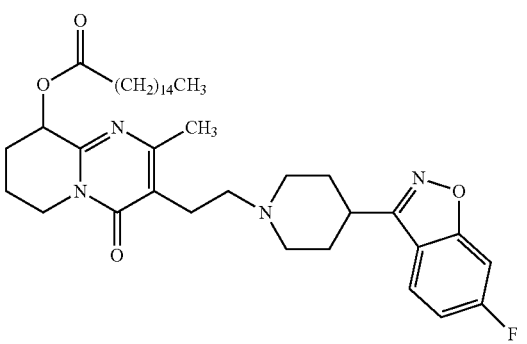

II

Paliperidone palmitate is psychotropic agent and marketed in the United States under the trade name Invega Sustenna®. Paliperidone palmitate is indicated for the treatment of schizophrenia and is available in the dosage form of extended release injectable suspension for intramuscular administration.

Paliperidone and Paliperidone palmitate were described for the first time in the U.S. Pat. No. 5,158,952. The U.S. '952 discloses processes for the preparation of Paliperidone as well as decanoyl and acetyl esters of Paliperidone.

Various processes for preparing Paliperidone Palmitate are described in U.S. Pat. No. 6,077,843, U.S. Pat. No. 6,555,544, WO 2009/089076, WO 2012/164582, WO 2013/046225, IN 2383/CHE/2010, IN 3486/CHE/2012, IN 1685/MUM/2012, IN 113/MUM/2012, IN 2252/MUM/2011 and IN 3372/MUM/2012.

Like any other synthetic APIs, Paliperidone palmitate may contain extraneous compounds or impurities arising from the unreacted starting materials, by-products and/or degradation products. Impurities in API are undesirable and, in extreme cases, might even be harmful to a patient being treated with a dosage form of the API.

Further, solid state physical properties such as particle size of an active pharmaceutical ingredient (API) are very important in formulating a drug substance and can have profound effects on the ease and reproducibility of formulation. Small size of particles of Paliperidone Palmitate API is desired for the production of its extended-release injectable suspension.

The PCT application WO 2006/114384 discloses a process for preparing aseptic crystals of Paliperidone Palmitate having suitable particle size for using in the pharmaceutical composition. WO '384 discloses a process, which comprises steps of dissolving non-sterile Paliperidone Palmitate in ethyl alcohol, filtering the solution through sterile 0.22 μm filter, cooling the solution to room temperature to crystallize the product, reheating the suspension and cooling at a rate of 0.5° C./min to obtain aseptic crystals of Paliperidone palmitate.

However, this process is not suitable for industrial production of Paliperidone palmitate API as it involves repeated crystallization steps and lengthy process of cooling at slow rate to crystallize the product. Further, Paliperidone palmitate obtained by single crystallization from ethyl alcohol does not yield the Paliperidone palmitate of suitable particle size for using in extended-release injectable suspension.

Hence, there is a need in the art to develop a process for preparing aseptic Paliperidone Palmitate having a particle size suitable for use in the pharmaceutical composition.

OBJECTIVE OF THE INVENTION

The main objective of the present invention is to provide an improved process for the preparation of pure Paliperidone palmitate.

Another objective of the present invention is to provide a process for the preparation of aseptic Paliperidone palmitate having particle size suitable for use in pharmaceutical composition.

Yet another objective of the present invention is to provide an improved process for the preparation of aseptic Paliperidone Palmitate having particle size ($D_{90}$) less than 10 microns.

SUMMARY OF THE INVENTION

In one embodiment, the present invention provides a process for the preparation of pure Paliperidone Palmitate, which comprises:
a) providing a solution of Paliperidone Palmitate in an alcoholic solvent;
b) adding the alcoholic solution of Paliperidone palmitate to water or vice versa; and
c) isolating the product to obtain pure Paliperidone Palmitate.

In another embodiment, the present invention provides a process for the preparation of aseptic Paliperidone Palmitate, which comprises:
a) providing a solution of Paliperidone Palmitate in an alcoholic solvent;
b) filtering the obtained solution of Paliperidone palmitate through 0.2 micron filter;

c) adding the alcoholic solution of Paliperidone palmitate to water or vice versa;
d) filtering the product obtained from step (c); and
e) drying the product to obtain aseptic Paliperidone Palmitate.

In yet another embodiment, the present invention provides a process for the preparation of aseptic Paliperidone Palmitate having particle size ($D_{90}$) less than 10 micron, which comprises:
a) suspending Paliperidone Palmitate in an alcoholic solvent;
b) optionally, heating the obtained suspension to obtain clear solution;
c) filtering the solution of Paliperidone palmitate through 0.2 micron filter;
d) adding the alcoholic solution of Paliperidone palmitate to the pre-cooled water or vice versa;
e) filtering the obtained product; and
f) drying the product to obtain aseptic Paliperidone Palmitate having particle size ($D_{90}$) less than 10 micron.

In yet another embodiment, present invention relates to use of aseptic Paliperidone Palmitate prepared according to present invention in the extended-release injectable suspension.

DETAILED DESCRIPTION OF THE INVENTION

The present invention provides a process for the preparation aseptic Paliperidone Palmitate, which comprises:
a) providing a solution of Paliperidone Palmitate in an alcoholic solvent;
b) adding the alcoholic solution of Paliperidone palmitate to water or vice versa; and
c) isolating the product to obtain pure Paliperidone Palmitate.

In one aspect of the present invention, Paliperidone Palmitate is suspended in an alcoholic solvent and optionally heated the contents to obtain a clear solution.

The alcoholic solvent is lower alcohol selected from the group comprising of methanol, ethanol, n-propanol, isopropanol, n-butanol, isobutanol, tert-butanol or mixtures thereof.

The obtained solution of Paliperidone Palmitate is filtered through 0.2 micron filter to obtain a clear solution of Paliperidone Palmitate. The obtained solution of Paliperidone Palmitate is added to water in another flask to obtain a slurry solution.

In another way, water is added to the alcoholic solution of Paliperidone palmitate to obtain a slurry solution. The obtained slurry solution is filtered and kept under the suction to squeeze most of the filtrate. The obtained product is dried under reduced pressure to obtain pure Paliperidone Palmitate having particle size suitable for using in extended-release injectable suspension.

In another aspect of the present invention, the solution of Paliperidone Palmitate in an alcoholic solvent is obtained from a reaction mass containing Paliperidone Palmitate, wherein the reaction mass is obtained by reacting Paliperidone with palmitic acid or its derivatives selected from palmitoyl chloride or palmitic anhydride in an alcoholic solvent by methods known in the art. The reaction mass containing Paliperidone Palmitate in an alcoholic solvent is heated to obtain a clear solution. The obtained solution is filtered through a filter, preferably through 0.2 micron filter to obtain clear solution of Paliperidone Palmitate. The obtained solution is added to water to get slurry solution. In another way, water is added to the alcoholic solution of Paliperidone palmitate to obtain slurry solution. The obtained slurry solution is filtered and kept under suction to squeeze the most of the filtrate. The obtained product is dried by known methods, preferably under reduced pressure to obtain aseptic Paliperidone palmitate having particle size suitable for using in extended-release injectable suspension.

In one more aspect of the present invention, the Paliperidone Palmitate prepared according to present invention has a particle size suitable for using in extended-release injectable suspension. In the preferred aspect, at least 90% particles of the aseptic Paliperidone Palmitate prepared according to present invention have size ($D_{90}$) less than 10 microns.

The invention is illustrated with the following examples, which are provided by way of illustration only and should not be construed to limit the scope of the invention.

Example 1

Process for the Preparation of Aseptic Paliperidone Palmitate

Paliperidone Palmitate non-sterile (5 gm) was suspended in ethyl alcohol (90 ml) at 25° C.-30° C. and the contents were heated to 70° C.-75° C. to obtain a clear solution. The obtained contents were cooled to not less than 63° C. The above solution of Paliperidone palmitate was filtered through 0.2 microns filter in sterile area at not less than 63° C. and the filter was washed with pre-heated ethyl alcohol (10 ml, not less than 63° C.). The obtained clear solution was maintained at 65-70° C. In another flask DM water (50 ml) was cooled to 5-10° C. The above Paliperidone palmitate solution (in hot condition 65-70° C.) was added to the DM water over a period of 10-15 minutes and maintained the slurry solution for 60 minutes at 5-10° C. Filtered the slurry solution containing product at 5-10° C. and washed with ethyl alcohol (10 ml). The product was kept under suction to squeeze most of the filtrate and dried under reduced pressure (~25 mm Hg) at 50-55° C. till ethyl alcohol content is less than 4000 ppm to obtain title compound.

Yield: 4.55 g (0.91 w/w)

Particle Size: $D_{90}$=8.441 µm, $D_{50}$=2.805 µm & $D_{10}$=0.794 µm

Example 2

Process for the Preparation of Aseptic Paliperidone Palmitate

Paliperidone Palmitate non-sterile (5 gm) was suspended in ethyl alcohol (75 ml) at 25° C.-30° C. and the contents were heated to 70° C.-75° C. to obtain a clear solution. The solution of Paliperidone palmitate was cooled to not less than 63° C. and filtered through 0.2 microns filter in sterile area at not less than 63° C. and the filter was washed with pre-heated ethyl alcohol (5 ml, not less than 63° C.). The obtained clear solution was maintained at 65-70° C. DM water (50 ml) was added to the above solution over a period of 10-15 minutes at 65-70° C. and the slurry solution was maintained for 60 minutes at 5-10° C. The product was filtered at 5-10° C. and washed with ethyl alcohol (10 ml). The product was kept under suction to squeeze most of the filtrate and dried under reduced pressure (~25 mm Hg) at 50-55° C. till ethyl alcohol content is less than 4000 ppm to obtain title compound.

Yield: 4.6 g (0.92 w/w)

Particle Size: $D_{90}$=8.202, $D_{50}$=3.251 & $D_{10}$=0.809.

We claim:

1. A process for the preparation of pure Paliperidone Palmitate, which comprises:
   a) providing a solution of Paliperidone Palmitate in an alcoholic solvent;
   b) optionally, filtering the solution through micron filter;
   c) adding the alcoholic solution of Paliperidone palmitate to water or vice versa; and
   d) isolating the product to obtain pure Paliperidone Palmitate.

2. The process according to claim 1, wherein alcoholic solvent is selected from lower alcohols.

3. The process according to claim 1, wherein alcoholic solvent is selected from the group comprising of methanol, ethanol, n-propanol, isopropanol, n-butanol, isobutanol, tert-butanol or mixture thereof.

4. The process according to claim 1, wherein solution of Paliperidone Palmitate in an alcoholic solvent is prepared by suspending Paliperidone palmitate in an alcoholic solvent.

5. The process according to claim 1, wherein solution of Paliperidone palmitate is an alcoholic solvent is the solution obtained from the reaction mass containing Paliperidone palmitate and alcohol solvent.

6. The process according to claim 1, wherein solution of Paliperidone Palmitate in an alcoholic solvent is heated to obtain a clear solution.

7. The process according to claim 1, wherein solution of Paliperidone palmitate is filtered through 0.2 micron filter.

8. The process according to claim 1, wherein the obtained Paliperidone Palmitate has a particle size $D_{90}$ less than 10.

9. A process for the preparation of aseptic Paliperidone Palmitate having particle size ($D_{90}$) less than 10 micron, which comprises:
   a) suspending Paliperidone Palmitate in an alcoholic solvent;
   b) optionally, heating the obtained suspension to obtain clear solution;
   c) filtering the solution of Paliperidone palmitate through 0.2 micron filter;
   d) adding the alcoholic solution of Paliperidone palmitate to the pre-cooled water or vice versa;
   e) filtering the obtained product; and
   f) drying the product to obtain aseptic Paliperidone Palmitate having particle size ($D_{90}$) less than 10 micron.

* * * * *